United States Patent [19]

Pieler et al.

[11] Patent Number: 5,525,512
[45] Date of Patent: Jun. 11, 1996

[54] INCUBATOR

[75] Inventors: Christian Pieler; Franz E. Leichtfried, both of Vienna, Austria

[73] Assignee: Robocon Labor und Industrieroboterges m.b.H., Vienna, Austria

[21] Appl. No.: 211,889

[22] PCT Filed: Aug. 2, 1993

[86] PCT No.: PCT/AT93/00125

§ 371 Date: Jun. 28, 1994

§ 102(e) Date: Jun. 28, 1994

[87] PCT Pub. No.: WO94/04273

PCT Pub. Date: Mar. 3, 1994

[30] Foreign Application Priority Data

Aug. 18, 1992 [AT] Austria ................... 1662/92

[51] Int. Cl.$^6$ ............... C12M 1/02; C12M 1/38
[52] U.S. Cl. .......... 435/303.1; 435/809; 422/104; 422/65; 219/218; 219/385; 219/428
[58] Field of Search .......... 312/31, 31.2, 209, 312/283, 286; 219/218, 428, 385; 435/290, 316, 809, 283.1, 286.1, 286.2, 286.4, 286.6, 303.1, 303.2, 305.1, 305.2; 422/63–65, 104; 119/35, 37, 43

[56] References Cited

U.S. PATENT DOCUMENTS 3,205,033  9/1965  Stentz ..................... 219/218
3,715,148  2/1973  Beals ..................... 312/209
3,834,778  9/1974  Morrison et al. .......... 312/209
4,630,873  12/1986 Volker et al. ............ 312/209
4,720,463  1/1988  Farber et al. ............ 435/809
5,149,654  9/1992  Gross et al. ............. 435/809

FOREIGN PATENT DOCUMENTS 0195088  9/1986  European Pat. Off. .
0238313  9/1987  European Pat. Off. .
0429030  5/1991  European Pat. Off. .
8700087  1/1987  WIPO .
9308914  5/1993  WIPO .

*Primary Examiner*—William H. Beisner
*Attorney, Agent, or Firm*—Watson Cole Stevens Davis

[57] ABSTRACT

An incubator includes a housing (1) and a set (2) of shelves (3) for sample containers (8) containing cell cultures, for instance, positioned therein. In order to make it possible to use the incubator together with a robotic manipulator or similar device, the shelves (3) are fitted with guide elements (4) for the sample containers (8), the guide elements defining the relative positions of the sample containers. A door (6) in the front of the incubator permits access by a robotic manipulator. When the door (6) in the front of the incubator is closed, a door (6) in the rear of the incubator permits access to the inside of the incubator by operating personnel.

10 Claims, 2 Drawing Sheets

INCUBATOR

TECHNICAL FIELD

The invention relates to an incubator, especially for receiving sample containers, comprising a housing which can be opened on the front side, and a set of carrier trays which are disposed in the housing and are intended for the sample containers, which may or may not be removable.

STATE OF THE ART

There exist varying designs of such devices, where usually at least the inner temperature can be controlled or set to a specific value in accordance with the respective application. Especially with today's ever growing fields of application, for example, in clinical diagnostics, in quality control laboratories of the pharmaceutical industry, in pharmaceutical research and development and in biotechnology, higher demands are being made, however, on the quality of the inner atmosphere, which can correspondingly also be controlled, for example, with respect to its composition, moisture or proportion of different components.

With respect to the aforementioned fields of application there has also existed since the increased employment of handling robots the need to use such automatic machines also for constantly repeating handling steps, a state that causes a number of problems, not least also with regard to the incubators that are used. These problems could be solved only unsatisfactorily to date with the known devices of the aforementioned kind. Thus, for example, the necessary access to the interior of the incubator for the purpose of charging with the sample containers or removing in the interim for manipulating the content of the individual sample containers was difficult, insofar as such steps were supposed to be possible, on the one hand, manually via an operator and, on the other hand, automatically via the handling robot, during which procedure, however, any risk of an accident has to be ruled out in any case. Since the incubator is usually charged initially by hand at the start of a test cycle, a simple, fast and exact positioning of the individual sample containers relative to the handling robot must be possible a feature that cannot, however, be guaranteed with the prior art devices.

SUMMARY OF THE INVENTION

The object of the present invention is to improve an incubator of the aforementioned kind in such a manner that the aforementioned drawbacks of such known devices are avoided and that an advantageous use is also possible in a simple manner and precisely with respect to a handling robot.

The problem is solved with an incubator of the aforementioned kind in accordance with the present invention in that the carrier trays exhibit guide elements for the sample containers, which partially envelop the sample containers shape-lockingly and fix their relative position. Thus, even if the individual sample containers are inserted by hand, an accurate positioning of the same relative to the handling robot can be guaranteed in a simple manner without having to take complicated and protracted precautionary measures that would only prolong unnecessarily the sequence, for example, of a test cycle.

According to another especially preferred embodiment of the invention, the guide elements can form slide-in vats, which are open on the front and rear side, for the sample containers, whereby the front and rear side has one door each, whose two contact surfaces rest in the closed state against the sample containers and thus fix their position in the slide-in vats. Thus, apart from the customary front-sided door, the interior of the incubator is also accessible by way of a rear-sided door, a feature that allows the work area of a handling robot, accessing the interior, for example, via the front door, to be separated from the work area of an operator, accessing the interior of the incubator via the rear-sided door. After the operator has placed the individual sample containers into the slide-in vats, the position of the sample containers can be determined with accuracy by simply closing the door or both doors, so that the handling robot, which subsequently accesses the sample containers at some arbitrary time after the door allocated to the robot has been opened, finds the individual sample containers in a precisely defined positioned.

With respect to the latter state, another embodiment of the invention is especially advantageous, according to which the contact surfaces (7) are designed elastically on the side of one of the two doors (6), since it enables a reliable and accurate placing of the sample containers while compensating for the dimensional tolerances. The elastic contact surfaces or elements are provided preferably, of course, on the side of the handling robot, since then it can find the sample containers in any case in a rigidly defined form after the appropriate door has been opened.

Another embodiment of the invention provides that both doors can be operated via preferably pneumatic operating elements and a joint control, whereby it is possible to open one door only if the other door is closed. This feature further increases, on the one hand, the operating safety of the incubator and also ensures, on the other hand, that the handling robot cannot access, for example, a sample container, which is not yet centered by means of the two closed doors and then under some circumstances is not held correctly and can cause malfunctions in the cycle.

In another preferred embodiment of the invention the carrier trays are arranged with the guide elements in a shelf-like holding frame, which rests on support regions on the housing and whose position and/or orientation can be adjusted relative to the housing. Thus, the common position of all carrier trays can be adjusted to a certain extent relative to the housing of the incubator or also a handling robot, a feature that allows, for example, compensation for the assembly and set-up tolerances and the like.

With respect to the latter state the housing itself can also be equipped externally in an advantageous manner with preferably adjustable supports for the purpose of assembly and attachment to a base, a feature that allows, for example, the unevennesses of the assembly site or the like to be taken largely into consideration.

According to an especially preferred embodiment of the invention it is provided that, in order to receive the sample containers as microtiter plates exhibiting square outer edges, the guide elements are formed by essentially rectangular guide strips which extend continuously over the depth of the carrier trays and whose width corresponds in essence to the lateral distance between the microtiter plates and which are fastened, preferably cemented, to the otherwise flat carrier trays. The so-called microtiter plates are storage and reaction vessels for liquid samples. Width and length (127.7×85.4 mm) of the microtiter plates are standardized; however, there are models of different heights. They can be made of polypropylene, polystyrene, polycarbonate or other plastic materials; they can be transparent or opaque and used with or without cover. Some shape details of the microtiter plates can vary between the individual manufacturers, such as the height of the base; some manufacturers also chamfer two of the four corners of the microtiter plate and the related cover, so that these plates can be used only with the covers of the same manufacturer. In other makes of microtiter plates the base is raised in the center of the plate. Sample cups are lowered from the top into the microtiter plates; in the most customary configuration said sample cups are arranged in a matrix of 8×12 cups, which amounts to a total of 96 cups. However, there are also similar sample containers of the same length and width that contain only 48, 24, 12 or 6 cups, wherein the individual cup diameters are correspondingly larger.

Microtiter plates are most frequently use in the fields of clinical diagnostics, where they are used, e.g., for the ELISA process (enzyme-linked immuno assay), e.g., in blood banks; in quality control laboratories in the pharmaceutical industry, where they are used to test raw materials and products for maximum purity, e.g., in the so-called Limulus process; in pharmaceutical research and development; and in biotechnology, where they are used in so-called screening methods, wherein from a large number of test substances those with the desired clinical-therapeutic effect can be found. However, microtiter plates are also used in food chemistry and environmental chemistry.

The lateral distance between the individual microtiter plates that is defined by the width of the guide strips and the distance between the individual carrier trays is defined at the bottom in essence only by means of the dimension required with respect to the handling by means of the robot, thus resulting in a very high packing density and thus very good use of the interior of the incubator.

BRIEF DESCRIPTION OF THE DRAWINGS

The invention is explained in detail in the following with reference to the embodiment shown diagrammatically in the drawings.

DETAILED DESCRIPTION OF THE PREFERRED EMBODIMENTS

Figure 1:
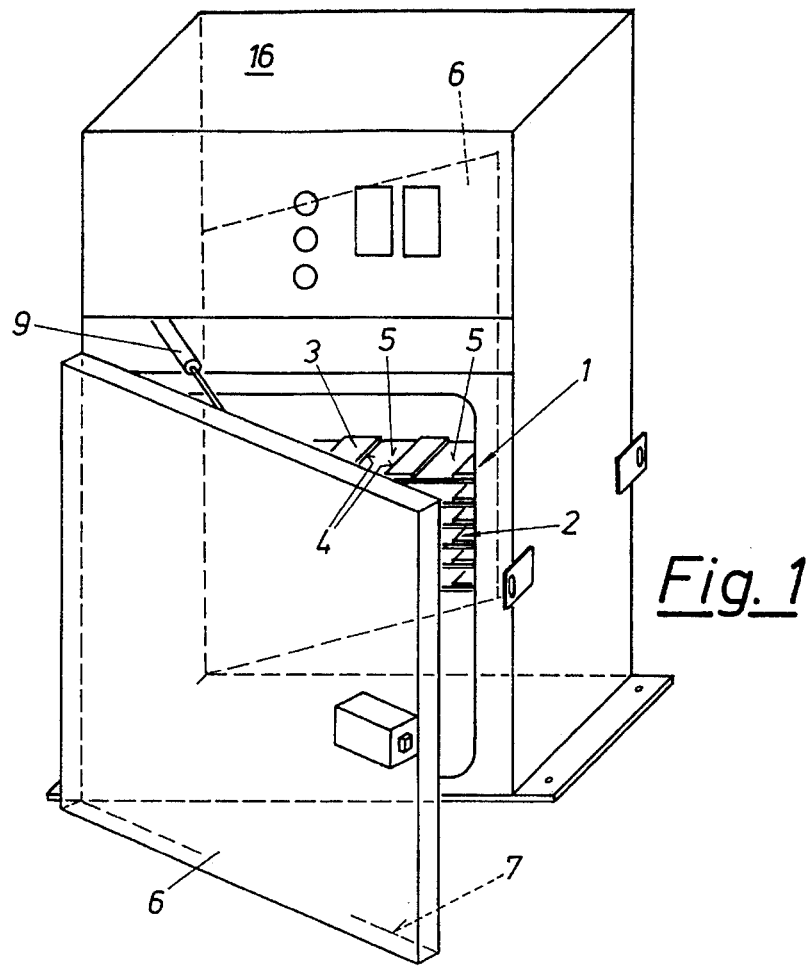
FIG. 1 is a perspective view of an incubator according to the invention.

The incubator which is depicted in FIG. 1 and intended to hold, for example, living cell cultures, exhibits a housing 1 and a set 2 of carrier trays 3 for sample containers that exhibit the cell cultures and are not depicted here; the set of carrier trays are arranged in the housing. The carrier trays 3 have guide elements 4 for the noted sample containers shape-lockingly as slide-in vats 5, which are open in the front and the rear, and determine the relative position of the sample containers in the incubator.

The front and rear side has one door 6 each that in the closed state (see also FIG. 3) rests with contact surface 7 on both sides against the sample containers (8 in FIG. 3) and thus also determine their position in the slide-in direction in the slide-in vats.

Both doors 6 can be operated by means of, e.g., pneumatic operating elements 9, which are shown at the front sided door 6 in FIG. 1, and a joint control (not illustrated here), wherein the control occurs preferably in such a manner that one door 6 can be opened only if the other door 6 is closed. In this manner it can be provided, for example, that a handling robot (also not illustrated here) has access to the interior or the incubator or the sample containers 8 by way of the front-sided door, whereas—when the front sided door is closed—an operator has access to the sample containers 8 by way of the rear sided door 6 and can put in or take out the sample containers.

Figure 2:
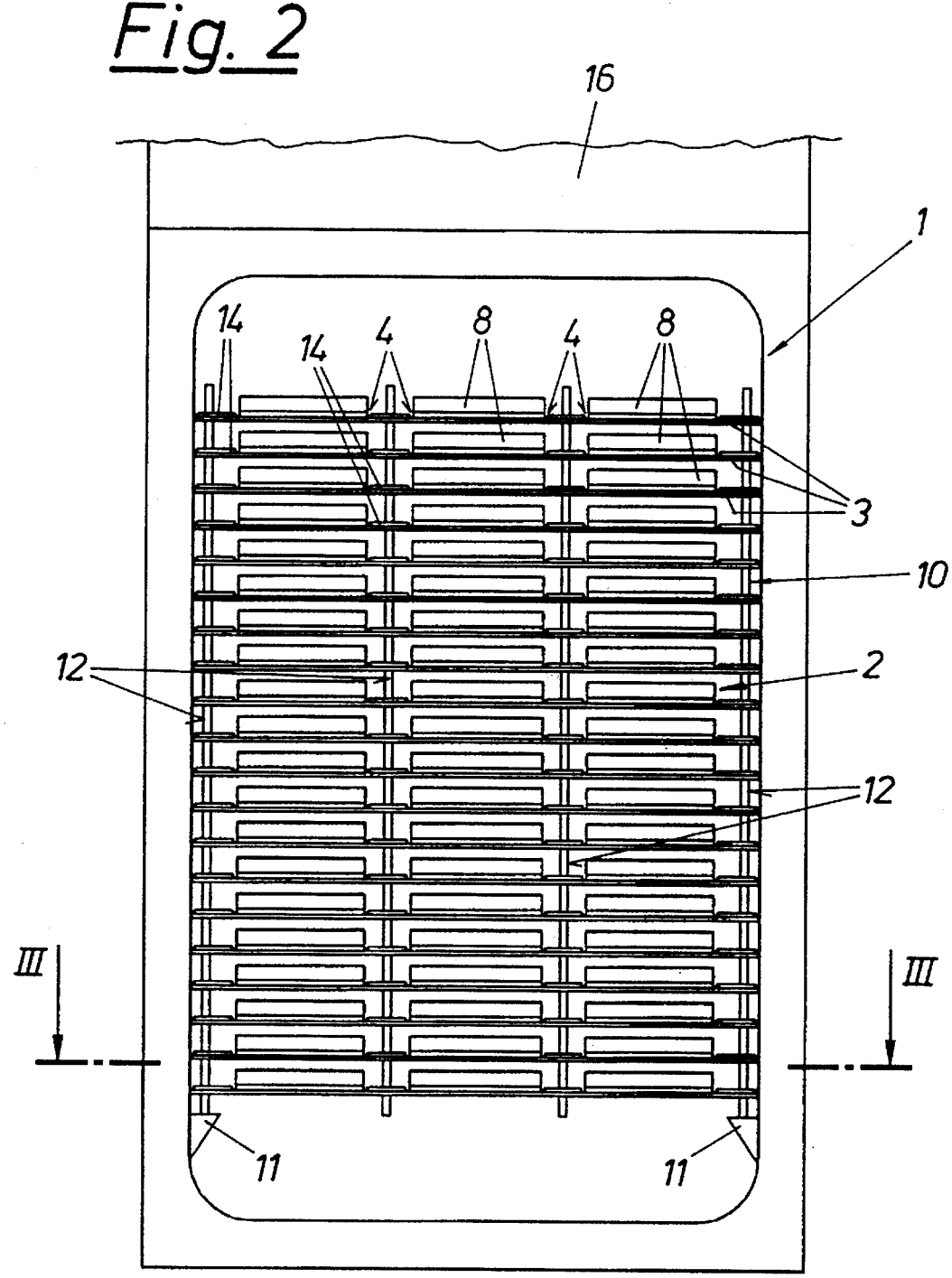
FIG. 2 is a partial top view of another embodiment from the front with the door removed.

The carrier trays 3 are arranged, as apparent especially in FIG. 2, together with the guide elements 4 in a shelf-like holding frame 10, which rests on support regions 11 on the housing 1 and whose position and/or orientation can also be adjusted relative to the housing in a manner that is not shown here. The individual carrier trays 3 are assembled via vertical connections 12, which penetrate the corresponding holes 13 in the carrier trays and provide for the requisite vertical distance between the carrier trays 3.

In order to receive the sample container 8 (illustrated here) as microtiter plates that exhibit in essence a square outer contour, the guide elements 4 are formed by essentially rectangular guide strips 14 which are continuous over the depth of the carrier trays 3 and whose lateral width corresponds in essence to the lateral distance between the sample containers 8 or microtiter plates and which are fastened, preferably cemented, on the otherwise flat carrier trays 3.

Figure 3:
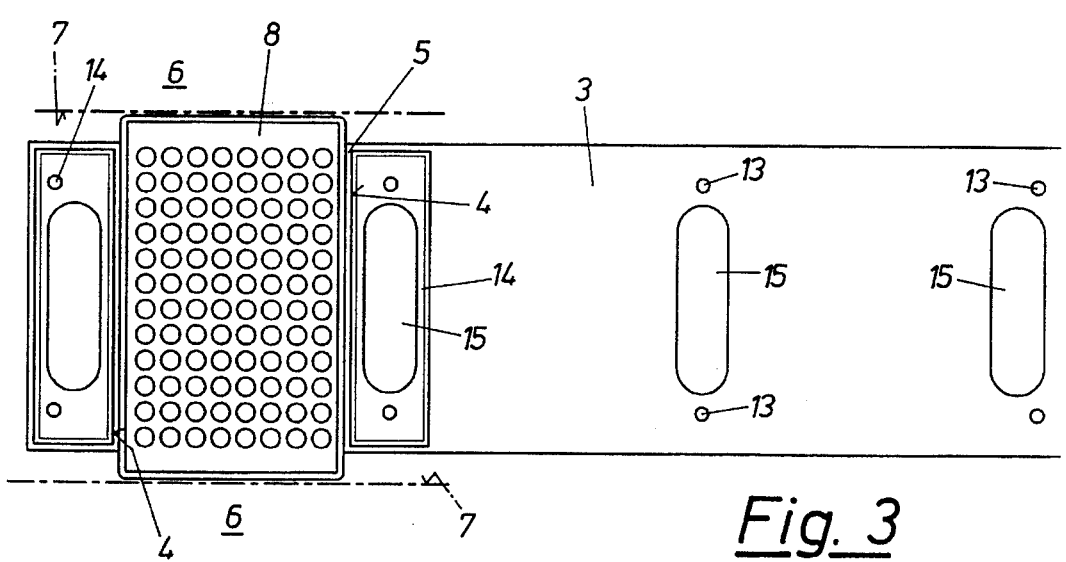
FIG. 3 is a partial view along the line III—III in FIG. 2.

To also enable circulation of the inner atmosphere of the incubator between the embedded sample containers 8, the region of the guide strips 14 has, according to FIG. 3, oblong, hole-like recesses 15 in the guide strips 14 and in the carrier trays 3, thus allowing for flow channels which extend continuously over the height of the holding frame 10.

For the sake of completeness, it should be noted that the construction 16 on the top side of the housing 1 that is visible in FIG. 1 and 2 contains elements and systems that are not shown here in detail and that are intended for controlling, for example, the temperature, composition, and moisture of the inner atmosphere of the incubator; furthermore, such construction can also contain parts of the controller logic, the door actuation, and the like, a feature that enables an advantageous, at least partial independence from a central control. In this respect the connection, supply, control lines and the like are not illustrated.

Apart from the illustrated and described design of the incubator according to the invention for receiving microtiter plates or similar square-shaped samples containers, a corresponding design, such as for Petri dishes, tissues culture surfaces and the like is also possible naturally within the scope of the invention, where in essence only the shape and arrangement of the guide elements have to be suitably changed.

We claim:

1. An incubator in which sample containers can be placed, said incubator comprising a housing having a front door on a first side thereof and a rear door on an opposite second side thereof, each of said front and rear doors defining an inner side which faces an interior of said housing when closed against said housing; and a set of carrier trays positioned in the interior of said housing, each of said set of carrier trays including a plurality of spaced apart guide elements which provide slide-in channels for sample containers, said slide-in channels being open towards said first and second sides of said housing; said inner side of each of said front and rear doors being capable of contacting and adjusting the positioning of sample containers located in said slide-in channels when each of said doors is closed.

2. An incubator as claimed in claim 1, wherein the inner side of at least one of said front and rear doors is elastic.

3. An incubator as claimed in claim 1, including pneumatic operating means connected to each of said front and rear doors for opening and closing thereof.

4. An incubator as claimed in claim 1, including a holding frame positioned in the interior of said housing, said holding frame mounting said carrier trays.

5. An incubator as claimed in claim 4, wherein said carrier trays are essentially flat and generally horizontally mounted one above another by said frame.

6. An incubator as claimed in claim 4, wherein said housing includes support means for supporting said frame at an adjustable orientation within said housing.

7. An incubator according to claim 1, wherein said guide elements are constructed as rectangular guide strips which continuously extend along a carrier tray in a direction between said first and second sides of said housing, said rectangular guide strips being spaced apart to receive microtiter plates having square outer edges therebetween.

8. An incubator according to claim 1, wherein said guide elements are fastened to said carrier trays.

9. An incubator as claimed in claim 1, including means for supplying a controlled atmosphere to said interior of said housing.

10. The combination of an incubator and a plurality of sample containers which can be placed therein, said incubator comprising a housing having a front door on a first side thereof and a rear door on an opposite second side thereof, each of said front and rear doors defining an inner side which faces an interior of said housing when closed against said housing, and a set of carrier trays including a plurality of spaced apart guide elements which provide slide-in channels for said sample containers, said guide elements partially shape-lockingly enclosing said sample containers and being open towards said first and second sides of said housing; said inner side of each of said front and rear doors being capable of contacting and adjusting the positioning of sample containers in said slide-in channels when each of said doors is closed.

* * * * *